United States Patent
Kosaka et al.

(10) Patent No.: US 10,759,918 B2
(45) Date of Patent: **\*Sep. 1, 2020**

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventors: Shunsuke Kosaka, Kobe (JP); Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 282 days.

This patent is subject to a terminal disclaimer.

(21) Appl. No.: 15/201,830

(22) Filed: Jul. 5, 2016

(65) Prior Publication Data

US 2017/0037211 A1    Feb. 9, 2017

(30) Foreign Application Priority Data

Aug. 3, 2015 (JP) ................... 2015-153486

(51) Int. Cl.
| | |
|---|---|
| C08J 7/12 | (2006.01) |
| A61L 29/04 | (2006.01) |
| A61L 29/08 | (2006.01) |
| A61L 29/14 | (2006.01) |
| A61M 25/00 | (2006.01) |

(52) U.S. Cl.
CPC ............ C08J 7/123 (2013.01); A61L 29/042 (2013.01); A61L 29/085 (2013.01); A61L 29/14 (2013.01); A61L 29/145 (2013.01); A61M 25/0009 (2013.01); *C08J 2375/04* (2013.01); *C08J 2377/02* (2013.01); *C08J 2439/00* (2013.01); *C08J 2443/00* (2013.01)

(58) Field of Classification Search
CPC .................... C08J 7/123; C08L 51/04
See application file for complete search history.

(56) References Cited

U.S. PATENT DOCUMENTS

| | | |
|---|---|---|
| 3,418,066 A | 12/1968 | Caldwell et al. |
| 5,100,689 A | 3/1992 | Goldberg et al. |
| 5,154,727 A | 10/1992 | Dyer |
| 5,340,879 A | 8/1994 | Audenaert et al. |
| 5,443,511 A | 8/1995 | Ogawa et al. |
| 5,453,467 A | 9/1995 | Bamford et al. |
| 5,637,460 A | 6/1997 | Swan |
| 5,688,252 A | 11/1997 | Matsuda et al. |
| 5,688,747 A | 11/1997 | Khan et al. |
| 5,855,623 A | 1/1999 | English et al. |
| 5,858,545 A * | 1/1999 | Everaerts ........... C08F 290/148 428/447 |
| 5,885,566 A | 3/1999 | Goldberg |
| 5,889,073 A | 3/1999 | Zhang et al. |
| 5,954,869 A | 9/1999 | Elfersy et al. |
| 5,967,714 A | 10/1999 | Ottersbach et al. |
| 6,001,894 A | 12/1999 | Ottersbach et al. |
| 6,188,075 B1 | 2/2001 | Takayama et al. |
| 6,203,856 B1 | 3/2001 | Ottersbach et al. |
| 6,228,172 B1 | 5/2001 | Taylor et al. |
| 6,358,557 B1 | 3/2002 | Wang et al. |
| 6,458,867 B1 | 10/2002 | Wang et al. |
| 6,599,558 B1 | 7/2003 | Al-Lamee et al. |
| 6,808,738 B2 | 10/2004 | Ditizio et al. |
| 6,986,868 B2 | 1/2006 | Madsen |
| 7,160,592 B2 | 1/2007 | Rypacek et al. |
| 7,348,055 B2 | 3/2008 | Chappa et al. |
| 8,299,139 B1 | 10/2012 | Taranekar et al. |
| 8,323,750 B2 | 12/2012 | Yang et al. |
| 8,840,927 B2 | 9/2014 | Ditizio et al. |
| 9,339,845 B2 | 5/2016 | Minagawa |
| 9,469,736 B2 | 10/2016 | Minagawa |
| 9,758,605 B2 | 9/2017 | Minagawa |

(Continued)

FOREIGN PATENT DOCUMENTS

| | | |
|---|---|---|
| CN | 1635915 A | 7/2005 |
| CN | 101372538 A | 2/2009 |

(Continued)

OTHER PUBLICATIONS

Ordian (Principles of Polymerization, 4th Ed., (2004)) p. 261.*
English machine translation of JP-2011-188908-A, published Sep. 29, 2011.
English machine translation of JP-7-100744-A, published Apr. 18, 1995.
U.S. Office Action dated Jan. 10, 2019 for U.S. Appl. No. 15/036,100.
Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report issued in PCT/JP2013/074219 dated Dec. 3, 2013.

(Continued)

*Primary Examiner* — Kuo Liang Peng
(74) *Attorney, Agent, or Firm* — Birch, Stewart, Kolasch & Birch, LLP

(57) ABSTRACT

Methods are provided for surface-modifying a rubber vulcanizate or a thermoplastic elastomer. The methods allow these rubber vulcanizate or thermoplastic elastomer objects to have a lubricating surface layer chemically fixed thereon, instead of having a resin coating which has drawbacks such as a reduction in lubricity due to e.g. separation or peeling of the coating during movement within a vessel or tract. The present invention relates to a method for surface-modifying an object made of a rubber vulcanizate or a thermoplastic elastomer, the method including: step 1 of forming polymerization initiation points on a surface of the object; and step 2 of radically polymerizing a monomer starting from the polymerization initiation points by irradiation with ultraviolet light having a wavelength of 300 to 400 nm in the presence of an alkali metal salt to grow polymer chains on the surface of the object.

14 Claims, 1 Drawing Sheet

(56) References Cited

U.S. PATENT DOCUMENTS

| | | | |
|---|---|---|---|
| 9,982,105 B2 | 5/2018 | Minagawa | |
| 2002/0002363 A1 | 1/2002 | Urakawa et al. | |
| 2002/0161065 A1 | 10/2002 | Ditizio et al. | |
| 2003/0139620 A1 | 7/2003 | Yamaguchi et al. | |
| 2004/0071909 A1 | 4/2004 | McGlothlin et al. | |
| 2004/0086568 A1 | 5/2004 | Ditizio et al. | |
| 2004/0106732 A1 | 6/2004 | Tsuji et al. | |
| 2005/0137355 A1 | 6/2005 | Buckanin et al. | |
| 2005/0168685 A1 | 8/2005 | Katagiri et al. | |
| 2006/0155057 A1 | 7/2006 | Hermeling et al. | |
| 2006/0207723 A1 | 9/2006 | Kuhn et al. | |
| 2007/0003592 A1 | 1/2007 | Hissink | |
| 2007/0048349 A1 | 3/2007 | Salamone et al. | |
| 2007/0116971 A1 | 5/2007 | Yoshikawa et al. | |
| 2007/0197681 A1 | 8/2007 | Lowery et al. | |
| 2007/0275171 A1 | 11/2007 | Dang et al. | |
| 2008/0016644 A1 | 1/2008 | Mizote et al. | |
| 2008/0103287 A1 | 5/2008 | Chino et al. | |
| 2008/0281396 A1 | 11/2008 | Ishida et al. | |
| 2008/0312377 A1 | 12/2008 | Schmidt et al. | |
| 2008/0317991 A1 | 12/2008 | Pieslak et al. | |
| 2009/0117303 A1* | 5/2009 | Goshiki | F16C 13/00 428/36.9 |
| 2009/0169715 A1 | 7/2009 | Dias et al. | |
| 2009/0239089 A1 | 9/2009 | Agata et al. | |
| 2009/0257022 A1 | 10/2009 | Abe et al. | |
| 2009/0280157 A1 | 11/2009 | Maas et al. | |
| 2009/0317443 A1 | 12/2009 | Willis et al. | |
| 2010/0053547 A1 | 3/2010 | Baude et al. | |
| 2010/0076546 A1 | 3/2010 | Dias et al. | |
| 2010/0247890 A1 | 9/2010 | Habassi et al. | |
| 2010/0255336 A1 | 10/2010 | Zabinski | |
| 2011/0086234 A1 | 4/2011 | Stasko et al. | |
| 2011/0124766 A1 | 5/2011 | Yang et al. | |
| 2011/0159101 A1 | 6/2011 | Kurdyumov et al. | |
| 2011/0160357 A1 | 6/2011 | Gerster et al. | |
| 2011/0263011 A1 | 10/2011 | Qiu et al. | |
| 2011/0274940 A1 | 11/2011 | Kyomoto et al. | |
| 2011/0313363 A1 | 12/2011 | D'Souza et al. | |
| 2012/0021151 A1 | 1/2012 | Tatarka et al. | |
| 2012/0100369 A1 | 4/2012 | Hanazawa et al. | |
| 2012/0324751 A1 | 12/2012 | Wakeman | |
| 2013/0158488 A1* | 6/2013 | Weaver | A61M 25/0043 604/264 |
| 2013/0158518 A1 | 6/2013 | Li et al. | |
| 2013/0188124 A1 | 7/2013 | Li et al. | |
| 2013/0203883 A1 | 8/2013 | Minagawa | |
| 2013/0274367 A1 | 10/2013 | Minagawa et al. | |
| 2013/0303689 A1 | 11/2013 | Sato et al. | |
| 2013/0310772 A1* | 11/2013 | Minagawa | C08C 19/28 604/265 |
| 2014/0039084 A1 | 2/2014 | Minagawa | |
| 2014/0128493 A1 | 5/2014 | Minagawa | |
| 2014/0322468 A1 | 10/2014 | Minagawa | |
| 2015/0203612 A1 | 7/2015 | Minagawa | |
| 2015/0329755 A1 | 11/2015 | Hakoshima et al. | |
| 2016/0122488 A1 | 5/2016 | Minagawa | |
| 2016/0213820 A1 | 7/2016 | Minagawa et al. | |
| 2016/0281216 A1 | 9/2016 | Shibusawa | |

FOREIGN PATENT DOCUMENTS

| | | |
|---|---|---|
| CN | 101565489 A | 10/2009 |
| CN | 102382291 A | 3/2012 |
| CN | 202427397 U | 9/2012 |
| CN | 102782056 A | 11/2012 |
| CN | 103193927 A | 7/2013 |
| CN | 103242553 A | 8/2013 |
| CN | 104119552 A | 10/2014 |
| EP | 0810239 A2 | 12/1997 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 4-250158 A | 9/1992 |
| JP | 5-43634 A | 2/1993 |
| JP | 5-76590 A | 3/1993 |
| JP | 5-115541 A | 5/1993 |
| JP | 5-179055 A | 7/1993 |
| JP | 6-25450 A | 2/1994 |
| JP | 6-510322 A | 11/1994 |
| JP | 7-47120 A | 2/1995 |
| JP | 7-100744 A | 4/1995 |
| JP | 7-289630 A | 11/1995 |
| JP | 8-1793 A | 1/1996 |
| JP | 9-31361 A | 2/1997 |
| JP | 9-67457 A | 3/1997 |
| JP | 9-180359 A | 4/1997 |
| JP | 10-231 A | 1/1998 |
| JP | 10-17688 A | 1/1998 |
| JP | 10-90500 A | 4/1998 |
| JP | 10-251350 A | 9/1998 |
| JP | 10-298320 A | 11/1998 |
| JP | 10-330383 A | 12/1998 |
| JP | 11-192305 A | 7/1999 |
| JP | 2000-273229 A | 10/2000 |
| JP | 2001-29452 A | 2/2001 |
| JP | 2001-31871 A | 2/2001 |
| JP | 2001-46956 A | 2/2001 |
| JP | 2001-95621 A | 4/2001 |
| JP | 2001-164176 A | 6/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2003-520107 A | 7/2003 |
| JP | 2004-528418 A | 9/2004 |
| JP | 2004-298220 A | 10/2004 |
| JP | 2005-3817 A | 1/2005 |
| JP | 2005-516736 A | 6/2005 |
| JP | 2005-186577 A | 7/2005 |
| JP | 2005-208290 A | 8/2005 |
| JP | 2005-213516 A | 8/2005 |
| JP | 2005-523981 A | 8/2005 |
| JP | 2005-253538 A | 9/2005 |
| JP | 2006-61273 A | 3/2006 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-196211 A | 8/2007 |
| JP | 2007-202965 A | 8/2007 |
| JP | 2008-73883 A | 4/2008 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-508541 A | 3/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2010-229180 A | 10/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2002-502286 A | 1/2012 |
| JP | 2012-6390 A | 1/2012 |
| JP | 2012-105579 A | 6/2012 |

(56) References Cited

FOREIGN PATENT DOCUMENTS

| | | |
|---|---|---|
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31428 A | 2/2014 |
| JP | 2014-31429 A | 2/2014 |
| JP | 2014-31430 A | 2/2014 |
| JP | 2014-108153 A | 6/2014 |
| JP | 2014-214226 A | 11/2014 |
| JP | 2015-502438 A | 1/2015 |
| JP | 2015-107312 A | 6/2015 |
| JP | 6034506 B2 | 11/2016 |
| WO | WO 93/05081 A1 | 3/1993 |
| WO | 9-313594 A | 12/1997 |
| WO | WO 01/52915 A1 | 7/2001 |
| WO | WO 01/60923 A1 | 8/2001 |
| WO | WO 03/022322 A2 | 3/2003 |
| WO | WO 031068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2008/023604 A1 | 2/2008 |
| WO | WO 2008/053712 A1 | 5/2008 |
| WO | WO 2009/009628 A2 | 1/2009 |
| WO | WO 2009/012353 A2 | 1/2009 |
| WO | WO 2009/085817 A1 | 7/2009 |
| WO | WO 2010/058848 A1 | 5/2010 |
| WO | WO 2010/131652 A1 | 11/2010 |
| WO | WO 2011/038483 A1 | 4/2011 |
| WO | WO 2011/047013 A1 | 4/2011 |
| WO | WO 2011/076924 A1 | 6/2011 |
| WO | WO 2012/091169 A1 | 7/2012 |
| WO | WO 2012/096320 A1 | 7/2012 |
| WO | WO 2012/165525 A1 | 12/2012 |
| WO | WO 2013/016849 A1 | 2/2013 |
| WO | WO 2014/148479 A1 | 9/2014 |
| WO | WO 2014/203668 A1 | 12/2014 |

OTHER PUBLICATIONS

International Search Report, dated Jul. 24, 2012, for International Application No. PCT/JP2012/064030.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.
U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action dated Jun. 24, 2015, for U.S. Appl. No. 14/118,136.
U.S. Office Action dated Sep. 21, 2015, for U.S. Appl. No. 14/107,746.
U.S. Office Action, dated Apr. 17, 2015, for U.S. Appl. No. 13/775,451.
U.S. Office Action, dated Aug. 25, 2014, for U.S. Appl. No. 13/956,974.
"Fundamental of Polymer Chemistry and Physics," edited by Wuji Wei and etc., Chemical Industry Press, Oct. 2011, pp. 59-60 (4 pages total).
English translation of Chinese Office Action for Appl. No. 201480032195.6 dated Jan. 24, 2018.
English translation of the Chinese Office Action, dated Sep. 22, 2017, for Chinese Application No. 201380044153.X.
International Search Report and English translation thereof, dated Jan. 21, 2014, for International Application No. PCT/JP2013/081090.
International Search Report and Written Opinion of the International Searching Authority, issued in PCT/JP2014/079947, dated Jan. 20, 2015.
International Search Report and English translation for PCT/JP2014/082367 dated Mar. 3, 2015.
International Search Report and English translation for PCT/JP2015/070547 (PCT/ISA/210) dated Oct. 6, 2015.
International Search Report, dated Feb. 25, 2014, for International Application No. PCT/JP2013/082409.
International Search Report, issued in PCT/JP2014/063268, dated Aug. 19, 2014.
Jinan Haohua Industry Co., Ltd., "Ethanaminum, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, http://guide7932.guidechem.com/pro-show2436647.html.
Placzek et al., "Photosensitizing properties of compounds related to benzophenone," Acta Dermato-Venereologica, vol. 93, No. 1, 2013, pp. 30-32.
U.S. Office Action, dated Nov. 3, 2016, for U.S. Appl. No. 14/896,096.
Written Opinion of the International Searching Authority and English translation for PCT/JP2015/070547 (PCT/ISA/237) dated Oct. 6, 2015.
Written Opinion of the International Searching Authority and English translation for PCT/JP2014/082367 (PCT/ISA/237) dated Mar. 3, 2015.
Zhang et al., "Corona Radiation Technology," China Textile Press, May 2003, p. 14 (3 pages total).
Arkles, "Hydrophobicity, Hydrophilicity and Silane Surface Modification", Gelest, Self-Assembled Monolayers (SAMs), Version 2.0, 2011, pp. 1-80 (84 pages total), XP-55098863.
Chin-Quee et al., "Endothelial Cell Recovery, Acute Thrombogenicity, and Monocyte Adhesion and Activation on Fluorinated Copolymer and Phosphorylcholine Polymer Stent Coatings," Biomaterials, vol. 31, 2010 (published online Oct. 12, 2009), pp. 648-657.
English translation of the Written Opinion of the International Searching Authority (Form PCT/ISA/237) for International Application No. PCT/JP2014/076887, dated Dec. 22, 2014.
International Search Report (Form PCT/ISA/210), issued in PCT/JP2014/076887, dated Dec. 22, 2014.
Partial English translation of Chinese Office Action for Chinese Application No. 201480054969.5, dated May 2, 2018.
Stasko et al., "Nitric oxide-releasing sol-gel coatings on titanium implants", SciFinder, Accession No. 2011: 467726, 2011, pp. 2-6 (5 pages).
Written Opinion of the International Searching Authority (Form PCT/ISA/237), issued in PCT/JP2014/076887, dated Dec. 22, 2014.
Xue et al., "Surface Modification and Physical Property Study of Inorganic Nanomaterials," 1st Edition, Hefei Industrial University Press, Oct. 31, 2009, pp. 122-123 (4 pages total).
Author Unknown, "tetra-n-propyl silicate", CAS Registry No. 682-01-9, SciFinder®, 2019, 1 page.
Author Unknown, "Unspecified", CAS Registry No. 308068-81-7, SciFinder®, 2019, p. 2 (1 page).
English machine translation of Japanese Publication No. 2001-164176-A.

* cited by examiner

SURFACE MODIFICATION METHOD AND SURFACE-MODIFIED ELASTIC BODY

TECHNICAL FIELD

The present invention relates to surface modification methods capable of providing surfaces which exhibit lubricity when wetted. The present invention also relates to surface-modified elastic bodies, such as surface-modified medical devices or catheters, at least part of whose surface has been modified by the surface modification methods.

BACKGROUND ART

Catheters used in medical and other fields, such as vascular catheters or urethral catheters for urethral catheterization, are inserted into blood vessels, digestive tracts, tracheae, bile ducts, or ureters and used in aqueous solutions like blood or body fluids. Therefore, they need to be able to be smoothly inserted without damaging tissues.

In order to satisfy this requirement, a low friction lubricant is applied to the surface of a catheter, or the surface of a catheter is coated with a lubricant layer before use (see Patent Literatures 1 to 3). However, unfortunately, these applied or coated lubricant layers have insufficient lubricity and, further, their lubricity is reduced due to e.g. their separation or peeling during movement within a vessel or a tract because these layers are not chemically fixed to the catheter surface.

CITATION LIST

Patent Literature

Patent Literature 1: JP 2011-188908 A
Patent Literature 2: JP 2009-518479 T
Patent Literature 3: JP H07-100744 B

SUMMARY OF INVENTION

Technical Problem

The present invention aims to solve the above problems and provide methods for surface-modifying a rubber vulcanizate or a thermoplastic elastomer. The methods allow these rubber vulcanizate or thermoplastic elastomer objects to have a lubricating surface layer chemically fixed thereon, instead of having a resin coating which has drawbacks such as a reduction in lubricity due to e.g. separation or peeling of the coating during movement within a vessel or a tract. The present invention also aims to provide surface-modified elastic bodies, such as surface-modified medical devices, e.g. catheters, and surface-modified mudguard fenders, at least part of whose surface has been modified by the surface modification methods.

Solution to Problem

The present invention relates to a method for surface-modifying an object made of a rubber vulcanizate or a thermoplastic elastomer, the method including: step 1 of forming polymerization initiation points on a surface of the object; and step 2 of radically polymerizing a monomer starting from the polymerization initiation points by irradiation with ultraviolet light having a wavelength of 300 to 400 nm in the presence of an alkali metal salt to grow polymer chains on the surface of the object.

The present invention also relates to a method for surface-modifying an object made of a rubber vulcanizate or a thermoplastic elastomer, the method including step I of radically polymerizing a monomer by irradiation with ultraviolet light having a wavelength of 300 to 400 nm in the presence of a photopolymerization initiator and an alkali metal salt to grow polymer chains on a surface of the object.

The step 1 preferably includes adsorbing a photopolymerization initiator onto a surface of the object, optionally followed by irradiation with ultraviolet light having a wavelength of 300 to 400 nm, to form polymerization initiation points from the photopolymerization initiator on the surface.

The photopolymerization initiator is preferably at least one of a benzophenone compound or a thioxanthone compound.

The method preferably includes introducing an inert gas into a reaction vessel, a reaction pipe, and a reaction solution during or before the light irradiation, and polymerizing the monomer in an atmosphere replaced with the inert gas.

The monomer is preferably an alkali metal-containing monomer.

The alkali metal-containing monomer is preferably at least one selected from the group consisting of alkali metal salts of acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, and styrenesulfonic acid.

The monomer is preferably a halogen-containing monomer. The halogen-containing monomer is preferably a nitrogen-containing monomer.

The nitrogen-containing monomer is preferably at least one of 2-(methacroyloxy)ethyl trimethylammonium chloride or 2-(acryloyloxy)ethyl trimethylammonium chloride.

The monomer is preferably a zwitterionic monomer.

The alkali metal salt is preferably at least one of sodium chloride or potassium chloride.

Preferably, a solution of the monomer, or the monomer in the liquid state contains a polymerization inhibitor, and is polymerized in the presence of the polymerization inhibitor.

The present invention relates to a surface-modified elastic body, produced by the surface modification method.

The present invention relates to a surface-modified elastic body, produced by the surface modification method, the elastic body being required to have lubricity in the presence of water.

The present invention relates to a surface-modified elastic body, including a three-dimensional solid body at least part of whose surface is modified by the surface modification method.

The present invention also relates to a catheter, at least part of whose surface is modified by the surface modification method.

Advantageous Effects of Invention

The methods for surface-modifying an object made of a rubber vulcanizate or a thermoplastic elastomer of the present invention include step 1 of forming polymerization initiation points on a surface of the object, and step 2 of radically polymerizing a monomer starting from the polymerization initiation points by irradiation with ultraviolet light having a wavelength of 300 to 400 nm in the presence of an alkali metal salt to grow polymer chains on the surface of the object; or include step I of radically polymerizing a monomer by irradiation with ultraviolet light having a wavelength of 300 to 400 nm in the presence of a photopolymerization initiator and an alkali metal salt to grow polymer chains on a surface of the object. The objects surface-modified by the methods have a lubricating polymer fixed to their surface. Thus, the methods of the present invention provide the surface with excellent lubricity and excellent lubricant durability to repeated movements, i.e. a durability such that there will be little reduction in lubricity. Accordingly, by forming polymer chains on the surface of the objects to be modified according to the methods of the present invention, it is possible to produce surface-modified elastic bodies, such as surface-modified catheters or mudguard fenders, which are excellent in those properties.

DESCRIPTION OF EMBODIMENTS

Figure 1:
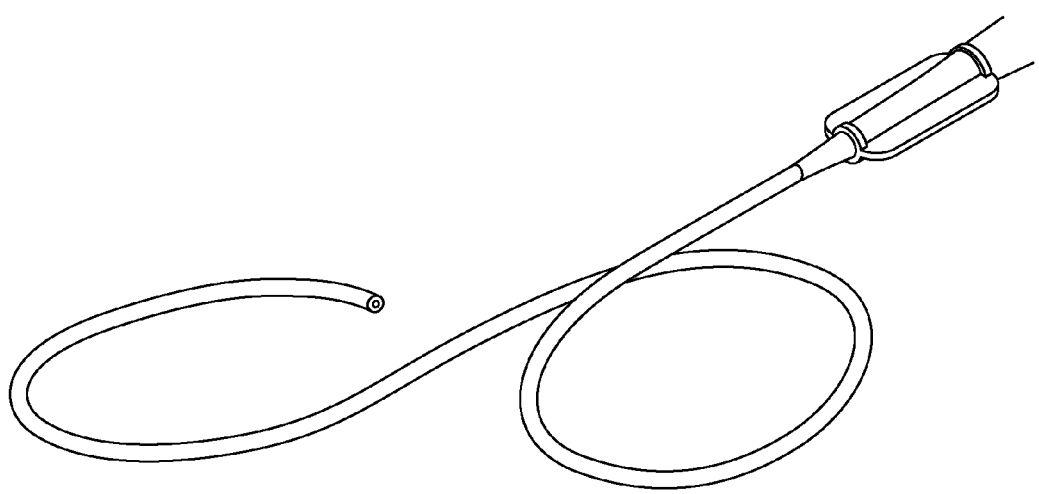
FIG. 1 is an exemplary schematic view of a vascular catheter.
Figure 2:
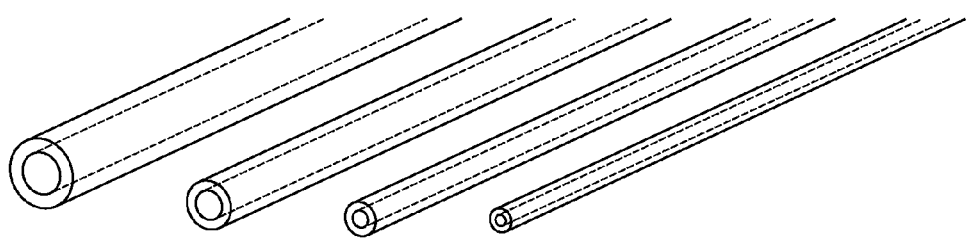
FIG. 2 is an exemplary schematic view showing catheters having different diameters.

The first aspect of the present invention is a method for surface-modifying an object made of a rubber vulcanizate or a thermoplastic elastomer, the method including: step 1 of forming polymerization initiation points on a surface of the object; and step 2 of radically polymerizing a monomer starting from the polymerization initiation points by irradiation with ultraviolet light having a wavelength of 300 to 400 nm in the presence of an alkali metal salt to grow polymer chains on the surface of the object.

In step 1, polymerization initiation points are formed on the surface of a formed rubber vulcanizate or a formed thermoplastic elastomer (an object to be modified). For example, the step 1 may be carried out by adsorbing a photopolymerization initiator onto the surface of the object to form polymerization initiation points, or by adsorbing a photopolymerization initiator onto the surface of the object and then irradiating the surface with ultraviolet light having a wavelength of 300 to 400 nm to form polymerization initiation points from the photopolymerization initiator on the surface.

Examples of thermoplastic elastomers that can be used as the object to be modified include nylon, polyester, polyurethane, polypropylene, acrylonitrile-butadiene-styrene copolymer resin (ABS), fluororesins such as polytetrafluoroethylene, and dynamically crosslinked thermoplastic elastomers prepared from these elastomers. Examples of nylon include nylon 6, nylon 66, nylon 11, and nylon 12. The dynamically crosslinked thermoplastic elastomer is preferably obtained by dynamically crosslinking a halogenated butyl rubber in a thermoplastic elastomer. Preferred examples of the thermoplastic elastomer used in this case include nylon, polyurethane, polypropylene, and styrene-isobutylene-styrene block copolymer (SIBS).

Examples of rubber vulcanizates that can be used as the object to be modified include natural rubber, deproteinized natural rubber, styrene-butadiene rubber, polybutadiene rubber, polyisoprene rubber, silicone rubber, and butyl rubber and halogenated butyl rubber which have a degree of unsaturation of a few percent of isoprene units.

The conditions for vulcanizing the rubber may be selected appropriately. The vulcanization temperature of the rubber is preferably 140° C. or higher, more preferably 170° C. or higher, still more preferably 175° C. or higher.

Examples of the photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

Preferred among carbonyl compounds serving as photopolymerization initiators are benzophenone and derivatives thereof (benzophenone compounds). For example, suitable are benzophenone compounds represented by the following formula:

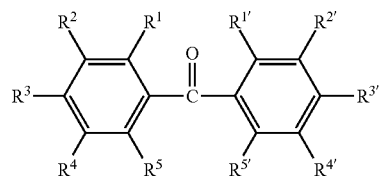

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxyl group, a primary to tertiary amino group, a mercapto group, or a hydrocarbon group that may contain an oxygen atom, a nitrogen atom, or a sulfur atom, and any two adjacent groups of $R^1$ to $R^5$ and $R^{1'}$ to $R^{5'}$ may be joined to each other to form a ring together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone as these compounds contribute to forming polymer brushes well.

The photopolymerization initiator may also suitably be a thioxanthone compound because it provides a high polymerization rate and can easily be adsorbed onto and/or reacted with rubber or the like. Suitable examples include compounds represented by the following formula:

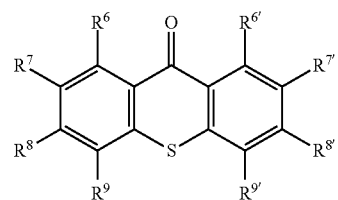

wherein $R^6$ to $R^9$ and $R^{6'}$ to $R^{9'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorption of a photopolymerization initiator such as a benzophenone or thioxanthone compound onto the surface of the object may be carried out as follows. In the case of a benzophenone or thioxanthone compound, for example, the benzophenone or thioxanthone compound is dissolved in an organic solvent to prepare a solution; a surface portion of the object to be modified is treated with this solution so that the compound is adsorbed on the surface portion; and, if necessary, the organic solvent is dried and evaporated off, whereby polymerization initiation points are formed. The surface-treating method may be any method that allows the solution of the benzophenone or thioxanthone compound to be brought into contact with the surface of the object to be modified. Suitable methods include applying or spraying the benzophenone or thioxanthone compound solution onto the surface; or immersing the surface into the solution. When only a part of the surface needs to be modified, it is sufficient to adsorb the photopolymerization initiator only onto the necessary part of the surface. In this case, for example, application or spraying of the solution is suitable. Examples of the organic solvent include methanol, ethanol, acetone, benzene, toluene, methyl ethyl ketone, ethyl acetate, and THF. Acetone is preferred because it does not swell the object intended to be modified, and it dries and evaporates quickly.

As described above, after the photopolymerization initiator is adsorbed on the surface of the object, the surface may further be irradiated with ultraviolet light having a wavelength of 300 to 400 nm to form polymerization initiation points from the photopolymerization initiator on the surface. This ultraviolet light irradiation can be carried out by known methods. For example, it may be carried out in the same manner as described for the ultraviolet light irradiation in step 2 which will be described later.

In step 2, a monomer is radically polymerized starting from the polymerization initiation points formed in step 1, by irradiation with ultraviolet light having a wavelength of 300 to 400 nm in the presence of an alkali metal salt to grow polymer chains on the surface of the object. In particular, by carrying out step 2 in the presence of an alkali metal salt, the polymer is sufficiently fixed to the surface of the object, and therefore excellent lubricity and excellent lubricant durability to repeated movements are imparted to the surface.

Examples of the alkali metal salt include halogenated alkali metal salts, alkali metal carbonates, alkali metal bicarbonates, alkali metal hydrogen carbonates, alkali metal nitrates, alkali metal sulfates, alkali metal bisulfates, alkali metal phosphates, alkali metal hydroxides, alkali metal acetates, alkali metal citrates, and alkali metal lactates. The alkali metal salt may be a water-soluble lithium, sodium, potassium, rubidium, or cesium salt.

Specific examples include sodium chloride, potassium chloride, cesium chloride, sodium bromide, potassium bromide, sodium nitrate, potassium nitrate, sodium carbonate, potassium carbonate, sodium sulfate, potassium sulfate, sodium bisulfate, potassium bisulfate (potassium hydrogensulfate), sodium phosphate, potassium phosphate, sodium hydroxide, potassium hydroxide, sodium hydrogen carbonate, sodium dihydrogen phosphate, disodium hydrogen phosphate, trisodium phosphate, sodium acetate, potassium acetate, sodium citrate, potassium citrate, sodium lactate, and potassium lactate. The alkali metal salts may be used alone or in combinations of two or more.

In view of lubricity and lubricant durability to repeated movements, halogenated alkali metal salts are preferred among these, and sodium chloride or potassium chloride is particularly preferred.

Suitable examples of the monomer include alkali metal-containing monomers (monomers each containing an alkali metal in the molecule), zwitterionic monomers (zwitterionic group-containing compounds: compounds each bearing a center of permanent positive charge and a center of negative charge), and halogen-containing monomers (monomers each containing a halogen in the molecule), which may be used alone or in combinations of two or more. If monomers simultaneously correspond to two or more of the above types, i.e. alkali metal-containing monomers, zwitterionic monomers, and halogen-containing monomers, as in the case of, for example, a monomer containing an alkali metal and a halogen (corresponding to both the alkali metal-containing monomer type and the halogen-containing monomer type), they are included in any of these two or more monomer types. The monomers may be used alone or in combinations of two or more.

Examples of the alkali metal-containing monomer include alkali metal salts of acrylic acid such as sodium acrylate and potassium acrylate; alkali metal salts of methacrylic acid such as sodium methacrylate and potassium methacrylate; alkali metal salts of itaconic acid such as sodium itaconate and potassium itaconate; alkali metal salts of 3-vinylpropionic acid such as sodium 3-vinylpropionate and potassium 3-vinylpropionate; alkali metal salts of vinylsulfonic acid such as sodium vinylsulfonate and potassium vinylsulfonate; alkali metal salts of 2-sulfoethyl (meth)acrylate such as sodium 2-sulfoethyl (meth)acrylate and potassium 2-sulfoethyl (meth)acrylate; alkali metal salts of 3-sulfopropyl (meth) acrylate such as sodium 3-sulfopropyl (meth) acrylate and potassium 3-sulfopropyl (meth)acrylate; alkali metal salts of 2-acrylamide-2-methylpropanesulfonic acid such as sodium 2-acrylamide-2-methylpropanesulfonate and potassium 2-acrylamide-2-methylpropanesulfonate; and alkali metal salts of styrenesulfonic acid such as sodium styrenesulfonate and potassium styrenesulfonate. Preferred among these is potassium 3-sulfopropyl methacrylate.

Examples of the zwitterionic monomer include carboxybetaines, sulfobetaines, and phosphobetaines. Compounds represented by Formula (1) below may also be mentioned, and compounds represented by Formula (2) below, among others, are suitable.

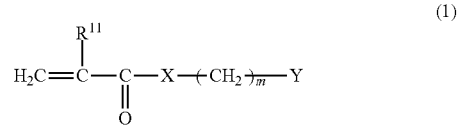
(1)

In the formula, $R^{11}$ represents —H or —$CH_3$; X represents —O—, —NH—, or —$N^+$—; m represents an integer of 1 or larger; and Y represents a zwitterionic group or a halogen group such as $Cl^-$, $Br^-$, or $F^-$.

In Formula (1), preferably, $R^1$ is —$CH_3$, X is —O—, and m is an integer of 1 to 10. In the zwitterionic group designated by Y, the cation may be a quaternary ammonium such as tetraalkylammonium, and the anion may be a carboxylate, sulfonate, or phosphate.

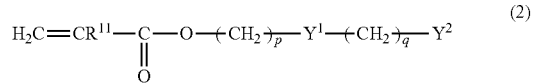
(2)

In the formula, $R^{11}$ represents —H or —CH$_3$; p and q each represent an integer of 1 or larger; and $Y^1$ and $Y^2$ represent ionic functional groups having electric charges opposite to each other.

In Formula (2), p is preferably an integer of 2 or larger, more preferably an integer of 2 to 10, and q is preferably an integer of 1 to 10, more preferably an integer of 2 to 4. Preferred examples of $R^{11}$ are the same as mentioned above. The symbols $Y^1$ and $Y^2$ are as described for the cation and anion above.

Typical suitable examples of the zwitterionic monomer include compounds represented by the following Formulas (2-1) to (2-4):

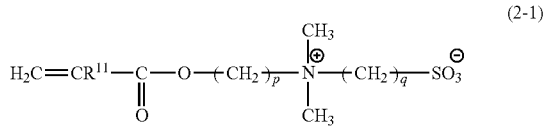
(2-1)

wherein $R^{11}$ represents a hydrogen atom or a methyl group, and p and q each represent an integer of 1 to 10,

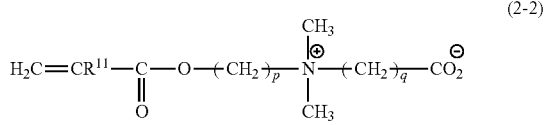
(2-2)

wherein $R^{11}$ represents a hydrogen atom or a methyl group, and p and q each represent an integer of 1 to 10,

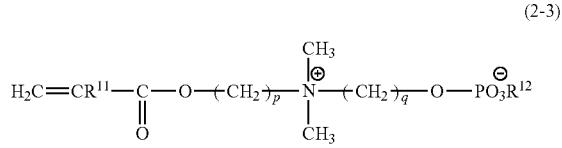
(2-3)

wherein $R^{11}$ represents a hydrogen atom or a methyl group; $R^{12}$ represents a C1-C6 hydrocarbon group; and p and q each represent an integer of 1 to 10, and

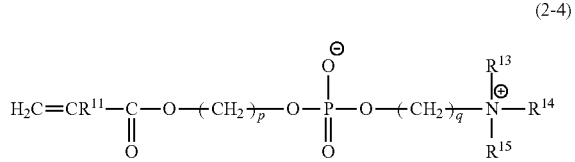
(2-4)

wherein $R^{11}$ represents a hydrogen atom or a methyl group; $R^{13}$, $R^{14}$, and $R^{15}$ are the same as or different from one another and each represent a C1 or C2 hydrocarbon group; and p and q each represent an integer of 1 to 10.

Examples of compounds represented by Formula (2-1) include dimethyl(3-sulfopropyl)(2-(meth)acryloyloxyethyl) ammonium betaine. Examples of compounds represented by Formula (2-2) include dimethyl(2-carboxyethyl)-(2-(meth) acryloyloxyethyl)ammonium betaine. Examples of compounds represented by Formula (2-3) include dimethyl (3-methoxyphosphopropyl)(2-(meth)acryloyloxyethyl)ammonium betaine. Examples of compounds represented by Formula (2-4) include 2-(meth)acryloyloxyethyl phosphorylcholine. Other zwitterionic monomers include 2-(meth) acryloyloxyethyl carboxybetaine, and 2-(meth)acryloyloxyethyl sulfobetaine. Among these, 2-(meth)acryloyloxyethyl phosphorylcholine is particularly preferred because of its high biocompatibility, i.e. low protein adsorbability.

The halogen-containing monomer refers to a monomer containing a halogen atom in the molecule. The halogen-containing monomers may be used alone or in combinations of two or more.

In view of lubricity and lubricant durability, the halogen-containing monomer may suitably be a nitrogen-containing monomer (halogen- and nitrogen-containing monomer). Specific preferred examples of such monomers include compounds represented by the following Formula (I):

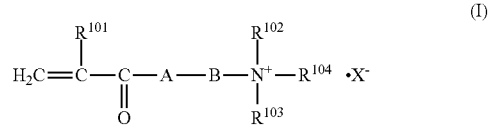
(I)

wherein A represents an oxygen atom or NH; B represents a C1-C4 alkylene group; $R^{101}$ represents a hydrogen atom or a methyl group; $R^{102}$, $R^{103}$, and $R^{104}$ are the same as or different from one another and each represent a C1-C4 alkyl group; and X$^-$ represents a halogen ion.

The symbol A is preferably an oxygen atom. The symbol B may be a linear or branched alkylene group such as a methylene group, an ethylene group, or a propylene group, with a methylene group or an ethylene group being preferred among these. Each of $R^{102}$ to $R^{104}$ may be a linear or branched alkyl group such as a methyl group, an ethyl group, or a propyl group, with a methyl group or an ethyl group being preferred among these. The symbol X (halogen atom) may be fluorine, chlorine, bromine or the like, preferably chlorine.

Examples of nitrogen-containing monomers represented by Formula (I) include 2-(methacroyloxy)ethyl trimethylammonium chloride (2-(methacroyloxy)ethyl trimethylaminium chloride), 2-(acryloyloxy)ethyl trimethylammonium chloride (2-(acryloyloxy)ethyl trimethylaminium chloride), 2-(methacroyloxy)ethyl dimethylethylammonium chloride (2-(methacroyloxy)ethyl dimethylethylaminium chloride), and 2-(acryloyloxy)ethyl dimethylethylammonium chloride (2-(acryloyloxy)ethyl dimethylethylaminium chloride).

The radical polymerization of a monomer in step 2 may be carried out, for example, as follows: a solution of an alkali metal salt and a monomer or a mixture of an alkali metal salt and a liquid monomer is applied (sprayed) onto the surface of the object on which a benzophenone or thioxanthone compound or the like has been adsorbed, or the object is immersed in a solution of an alkali metal salt and a monomer or a mixture of an alkali metal salt and a liquid monomer; and then the object is irradiated with ultraviolet light to allow radical polymerization (photoradical polymerization) of the monomer to proceed, whereby polymer chains are grown on the surface of the object. After the application, the surface of the object may further be covered with a transparent cover of glass, PET, polycarbonate or other materials, followed by irradiating the covered surface with ultraviolet light to allow radical polymerization (photoradical polymerization) of the monomer to proceed, whereby polymer chains are grown on the surface of the object.

The solvent for application (spraying), the method for application (spraying), the method for immersion, the conditions for irradiation, and the like may be conventionally known materials or methods. The solution of the radically polymerizable monomer may be an aqueous solution, or a solution in an organic solvent that does not dissolve the photopolymerization initiator (e.g. benzophenone or thioxanthone compound) used. Moreover, the solution of the radically polymerizable monomer or the liquid radically polymerizable monomer may contain a known polymerization inhibitor such as 4-methylphenol.

In the present invention, the radical polymerization of the monomer is allowed to proceed by light irradiation after the application of the monomer solution or the liquid monomer, or after the immersion in the monomer solution or the liquid monomer. In the light irradiation, ultraviolet light sources with an emission wavelength mainly in the ultraviolet region, such as high-pressure mercury lamps, metal halide lamps, and LED lamps, can be suitably used. The light dose may be selected appropriately in view of polymerization time and uniform progress of the reaction. Moreover, in order to prevent inhibition of polymerization due to active gas such as oxygen in the reaction vessel and the reaction pipe, oxygen is preferably removed from the reaction vessel, the reaction pipe, and the reaction solution during or before the light irradiation. To this end, appropriate operations may be performed; for example, an inert gas such as nitrogen gas or argon gas is introduced into the reaction vessel, the reaction pipe, and the reaction solution to discharge active gas such as oxygen from the reaction system and replace the atmosphere in the reaction system with the inert gas. Furthermore, in order to prevent inhibition of the reaction due to oxygen and the like, for example, a measure may appropriately be taken in which an ultraviolet light source is placed such that an air layer (oxygen content: 15% or higher) does not exist between the reaction vessel made of glass, plastics or the like and the reaction solution or the object intended to be modified.

The ultraviolet light has a wavelength of 300 to 400 nm. Such a wavelength enables polymer chains to be formed well on the surface of the object. Examples of light sources that can be used include high-pressure mercury lamps, LEDs with a center wavelength of 365 nm, LEDs with a center wavelength of 375 nm, and LEDs with a center wavelength of 385 nm. More preferred is irradiation with LED light having a wavelength of 355 to 390 nm. In particular, for example, LEDs with a center wavelength of 365 nm, which is close to the excitation wavelength (366 nm) of benzophenone, are preferred in view of efficiency. Light having a wavelength of less than 300 nm can cleave and damage molecules of the object intended to be modified. For this reason, light having a wavelength of 300 nm or greater is preferred. More preferred is light having a wavelength of 355 nm or greater because it produces very little damage to the object. In contrast, light having a wavelength of greater than 400 nm is less likely to activate the polymerization initiator, so that the polymerization reaction does not readily proceed. For this reason, light having a wavelength of 400 nm or less is preferred. Although LED light is suitable because the wavelength range of LED light is narrow so that no wavelengths other than the center wavelength are emitted, a mercury lamp or the like can also achieve similar effects to those of LED light if a filter is used to block light with wavelengths less than 300 nm.

In the present invention, polymer chains can be produced with good productivity by reducing the duration of irradiation with light having a wavelength of 300 to 400 nm. For example, the duration of the light irradiation may be 3 to 120 minutes, or may be reduced to 5 to 100 minutes, and even to 10 to 60 minutes.

The second aspect of the present invention is a method for surface-modifying an object made of a rubber vulcanizate or a thermoplastic elastomer, the method including step I of radically polymerizing a monomer by irradiation with ultraviolet light having a wavelength of 300 to 400 nm in the presence of a photopolymerization initiator and an alkali metal salt to grow polymer chains on a surface of the object. Specifically, by radically polymerizing a monomer by irradiation with ultraviolet light in the presence of a photopolymerization initiator as an initiator and, further, an alkali metal salt, a surface-modified elastic body can be produced on which a polymer layer (polymer) is fixed to the surface of the object to be modified. The object to be modified, the photopolymerization initiator, the alkali metal salt, and the monomer used in step I may be the same as those described above.

For example, step I may be carried out as follows: a photopolymerization initiator, an alkali metal salt, and a monomer are brought into contact with the surface of the object to be modified, and then the surface is irradiated with LED light having a wavelength of 300 to 400 nm to form polymerization initiation points from the photopolymerization initiator while simultaneously radically polymerizing the monomer starting from the polymerization initiation points in the presence of the alkali metal salt to grow polymer chains.

The radical polymerization of a monomer in step I may be carried out as follows: a solution of a monomer or a liquid monomer which contains a photopolymerization initiator such as a benzophenone or thioxanthone compound and an alkali metal salt is applied (sprayed) onto the surface of the object to be modified, or the object is immersed in a solution of a monomer or a liquid monomer which contains a photopolymerization initiator and an alkali metal salt; and then the object is irradiated with ultraviolet light to allow radical polymerization (photoradical polymerization) of the monomer to proceed, whereby polymer chains are grown on the surface of the object. Further, the surface of the object may be covered with a transparent cover of glass, PET, polycarbonate or other materials, followed by irradiating the covered surface with ultraviolet light as described hereinabove. The solvent for application (spraying), the method for application (spraying), the method for immersion, the conditions for irradiation, and the like may be the materials or methods described hereinabove. Moreover, the duration of irradiation with light having a wavelength of 300 to 400 nm may be reduced to 3 to 120 minutes, to 5 to 100 minutes, and even to 10 to 60 minutes as described above.

In step 2 or step I, two or more types of monomers may be radically polymerized simultaneously. Moreover, multiple types of polymer chains may be grown on the surface of the object to be modified. In the surface modification methods of the present invention, the polymer chains may be crosslinked to one another. In this case, the polymer chains may be crosslinked to one another by ionic crosslinking, crosslinking by a hydrophilic group containing an oxygen atom, or crosslinking by a halogen group such as iodine.

The above-described surface modification methods can be applied to rubber vulcanizates or thermoplastic elastomers to produce surface-modified elastic bodies, for example surface-modified elastic bodies that are excellent in lubricity in the presence of water. The methods may also be applied to at least a part of a three-dimensional solid body (e.g. elastic body) to produce a surface-modified elastic body with modified properties. Furthermore, preferred examples of the surface-modified elastic body include polymer brushes. The term "polymer brush" means an assembly of graft polymer molecules obtained in the "grafting from" approach by surface-initiated living radical polymerization. The graft chains are preferably oriented in a direction substantially vertical to the surface of the object because then the entropy decreases to reduce the molecular mobility of the graft chains, thereby providing lubricity. Furthermore, semidilute or concentrated brushes having a brush density of 0.01 chains/nm$^2$ or higher are preferred.

The surface modification methods may also be applied to rubber vulcanizates or thermoplastic elastomers to produce medical devices, such as catheters, at least part of whose surface is modified. The modification is applied to the surface of medical devices such as catheters preferably at least at a portion that requires lubricity, and may be applied to the entire surface.

EXAMPLES

The present invention is more specifically described with reference to, but not limited to, examples below.

Example 1

A 3 wt % solution of benzophenone in acetone was applied to the surface of a thermoplastic elastomer tube made of nylon 12 so that benzophenone was adsorbed onto the surface, followed by drying.

Subsequently, the tube was immersed in an aqueous solution of potassium 3-sulfopropyl methacrylate (1.25 M) with sodium chloride added and adjusted at a concentration of 1.5 M in a glass reaction vessel. The reaction vessel was sealed with a rubber stopper, and argon gas was introduced and allowed to bubble through the solution for 120 minutes to remove oxygen. The glass reaction vessel was irradiated with LED light having a wavelength of 365 nm for 45 minutes while being rotated. Thus, radical polymerization was carried out to grow polymer chains on the surface of the nylon tube, whereby a surface-modified elastic body (polymer brush) was prepared.

Example 2

A 3 wt % solution of benzophenone in acetone was applied to the surface of a thermoplastic elastomer tube made of nylon 12 so that benzophenone was adsorbed onto the surface, followed by drying.

Subsequently, the tube was immersed in an aqueous solution of potassium 3-sulfopropyl methacrylate (1.25 M) with potassium chloride added and adjusted at a concentration of 0.75 M in a glass reaction vessel. The reaction vessel was sealed with a rubber stopper, and argon gas was introduced and allowed to bubble through the solution for 120 minutes to remove oxygen. The glass reaction vessel was irradiated with LED light having a wavelength of 365 nm for 50 minutes while being rotated. Thus, radical polymerization was carried out to grow polymer chains on the surface of the nylon tube, whereby a surface-modified elastic body (polymer brush) was prepared.

Example 3

A 3 wt % solution of 2,4-diethylthioxanthone in acetone was applied to the surface of a thermoplastic elastomer tube made of nylon 12 so that 2,4-diethylthioxanthone was adsorbed onto the surface, followed by drying.

Subsequently, the tube was immersed in an aqueous solution of potassium 3-sulfopropyl methacrylate (1.25 M) with sodium chloride added and adjusted at a concentration of 1.5 M in a glass reaction vessel. The reaction vessel was sealed with a rubber stopper, and argon gas was introduced and allowed to bubble through the solution for 120 minutes to remove oxygen. The glass reaction vessel was irradiated with LED light having a wavelength of 365 nm for 20 minutes while being rotated. Thus, radical polymerization was carried out to grow polymer chains on the surface of the nylon tube, whereby a surface-modified elastic body (polymer brush) was prepared.

Example 4

A surface-modified elastic body (polymer brush) was prepared as in Example 1, except that 2-methacryloyloxyethyl phosphorylcholine was used instead of potassium 3-sulfopropyl methacrylate.

Example 5

A surface-modified elastic body (polymer brush) was prepared as in Example 2, except that 2-methacryloyloxyethyl phosphorylcholine was used instead of potassium 3-sulfopropyl methacrylate.

Example 6

A surface-modified elastic body (polymer brush) was prepared as in Example 3, except that 2-methacryloyloxyethyl phosphorylcholine was used instead of potassium 3-sulfopropyl methacrylate.

Example 7

A surface-modified elastic body (a polymer brush in which polymer chains were grown on the surface of a polyurethane tube) was prepared as in Example 1, except that a polyurethane tube was used instead of the nylon tube.

Example 8

A 3 wt % solution of benzophenone in acetone was applied to the surface of a thermoplastic elastomer tube made of nylon 12 so that benzophenone was adsorbed onto the surface, followed by drying.

Subsequently, the tube was immersed in an aqueous solution of 2-(methacroyloxy)ethyl trimethylammonium chloride (1.25 M) with sodium chloride added and adjusted at a concentration of 1.5 M in a glass reaction vessel. The reaction vessel was sealed with a rubber stopper, and argon gas was introduced and allowed to bubble through the solution for 120 minutes to remove oxygen. The glass reaction vessel was irradiated with LED light (5 mW/cm$^2$) having a wavelength of 365 nm for 30 minutes while being rotated. Thus, radical polymerization was carried out to grow polymer chains on the surface of the nylon tube, whereby a surface-modified elastic body (polymer brush) was prepared.

Example 9

A 3 wt % solution of 2,4-diethylthioxanthone in acetone was applied to the surface of a thermoplastic elastomer tube made of nylon 12 so that 2,4-diethylthioxanthone was adsorbed onto the surface, followed by drying.

Subsequently, the tube was immersed in an aqueous solution of 2-(methacroyloxy)ethyl trimethylammonium chloride (1.25 M) with sodium chloride added and adjusted at a concentration of 0.75 M in a glass reaction vessel. The reaction vessel was sealed with a rubber stopper, and argon gas was introduced and allowed to bubble through the solution for 120 minutes to remove oxygen. The glass reaction vessel was irradiated with LED light (5 mW/cm$^2$) having a wavelength of 365 nm for 40 minutes while being rotated. Thus, radical polymerization was carried out to grow polymer chains on the surface of the nylon tube, whereby a surface-modified elastic body (polymer brush) was prepared.

Example 10

A 3 wt % solution of 2,4-diethylthioxanthone in acetone was applied to the surface of a thermoplastic elastomer tube made of nylon 12 so that 2,4-diethylthioxanthone was adsorbed onto the surface, followed by drying.

Subsequently, the tube was immersed in an aqueous solution of 2-(methacroyloxy)ethyl trimethylammonium chloride (1.25 M) with sodium chloride added and adjusted at a concentration of 1.5 M in a glass reaction vessel. The reaction vessel was sealed with a rubber stopper, and argon gas was introduced and allowed to bubble through the solution for 120 minutes to remove oxygen. The glass reaction vessel was irradiated with LED light (5 mW/cm$^2$) having a wavelength of 365 nm for 20 minutes while being rotated. Thus, radical polymerization was carried out to grow polymer chains on the surface of the nylon tube, whereby a surface-modified elastic body (polymer brush) was prepared.

Example 11

The surface of a thermoplastic elastomer tube made of nylon 12 was immersed in an aqueous solution of potassium 3-sulfopropyl methacrylate (1.25 M) with sodium chloride and benzophenone added and adjusted at concentrations of 1.5 M and 0.003 M, respectively, in a glass reaction vessel. The reaction vessel was sealed with a rubber stopper, and argon gas was introduced and allowed to bubble through the solution for 120 minutes to remove oxygen. The glass reaction vessel was irradiated with LED light having a wavelength of 365 nm for 90 minutes while being rotated. Thus, radical polymerization was carried out to grow polymer chains on the surface of the nylon tube, whereby a surface-modified elastic body (polymer brush) was prepared.

Comparative Example 1

A tube made of nylon 12 was used as it was.

Comparative Example 2

The surface of a tube made of nylon 12 was coated with a 5% solution of methyl vinyl ether-maleic anhydride (GANTREZ-AN 16 available from IPS) in methanol, and this coated tube was used. It should be noted that nylon 12 is a material often used for vascular catheters, and methyl vinyl ether-maleic anhydride is a typical lubricant to impart lubricity to surfaces.

Comparative Example 3

A 3 wt % solution of benzophenone in acetone was applied to the surface of a thermoplastic elastomer tube made of nylon 12 so that benzophenone was adsorbed onto the surface, followed by drying.

Subsequently, the tube was immersed in an aqueous solution of potassium 3-sulfopropyl methacrylate (1.25 M) in a glass reaction vessel. The reaction vessel was sealed with a rubber stopper, and argon gas was introduced and allowed to bubble through the solution for 120 minutes to remove oxygen. The glass reaction vessel was irradiated with LED light (5 mW/cm$^2$) having a wavelength of 365 nm for 210 minutes while being rotated. Thus, radical polymerization was carried out to grow polymer chains on the surface of the nylon tube, whereby a surface-modified elastic body (polymer brush) was prepared.

Comparative Example 4

A 3 wt % solution of benzophenone in acetone was applied to the surface of a thermoplastic elastomer tube made of nylon 12 so that benzophenone was adsorbed onto the surface, followed by drying.

Subsequently, the tube was immersed in an aqueous solution of potassium 3-sulfopropyl methacrylate (1.25 M) in a glass reaction vessel. The reaction vessel was sealed with a rubber stopper, and argon gas was introduced and allowed to bubble through the solution for 120 minutes to remove oxygen. The glass reaction vessel was irradiated with LED light (5 mW/cm$^2$) having a wavelength of 365 nm for 60 minutes while being rotated. Thus, radical polymerization was carried out to grow polymer chains on the surface of the nylon tube, whereby a surface-modified elastic body (polymer brush) was prepared.

Comparative Example 5

A surface-modified elastic body (polymer brush) was prepared as in Comparative Example 4, except that 2-methacryloyloxyethyl phosphorylcholine was used instead of potassium 3-sulfopropyl methacrylate.

Comparative Example 6

A surface-modified elastic body (polymer brush) was prepared as in Example 8, except that sodium chloride was not added.

Comparative Example 7

A surface-modified elastic body (polymer brush) was prepared as in Example 8, except that sodium chloride was not added, and the duration of irradiation was changed to 60 minutes.

Comparative Example 8

A surface-modified elastic body (polymer brush) was prepared as in Example 11, except that sodium chloride was not added.

The surface-modified elastic bodies prepared in the examples and the comparative examples were evaluated as follows.
(Lubricity)

Water was applied to the surface of the tube, and the sliding properties of the surface were subjectively evaluated by touching with a human finger. The subjective evaluation was carried out by ten persons according to a rating scale of 1-5, where a rating of 5 corresponds to a tube with good sliding properties, and a rating of 1 corresponds to a tube with poor sliding properties that do not allow the finger to slide on the surface. The average of the ratings was calculated.

(Lubricant Durability)

After water was applied to the surface of the tube, the tube was held between fingers and slid on the fingers. This cycle was repeated 100 times. Then, the subjective evaluation was again carried out by ten persons according to the rating scale for lubricity, and the average of the ratings and the rate of decrease from the initial lubricity were calculated.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Lubricity | 4.7 | 4.6 | 4.8 | 4.5 | 4.3 | 4.7 | 4.3 | 4.8 | 4.7 | 4.9 | 4.6 |
| Durability | 4.6 | 4.5 | 4.7 | 4.3 | 4.1 | 4.6 | 4.1 | 4.7 | 4.5 | 4.8 | 4.5 |
| Rate of decrease | 2.1% | 2.2% | 2.1% | 4.4% | 4.7% | 2.1% | 4.7% | 2.1% | 4.3% | 2.0% | 2.2% |

TABLE 2

| | Comparative Example | | | | | | | |
|---|---|---|---|---|---|---|---|---|
| | 1 | 2 | 3 | 4 | 5 | 6 | 7 | 8 |
| Lubricity | 1 | 4.2 | 4.6 | 2.1 | 1.5 | 4.7 | 2.7 | 1.9 |
| Durability | 1 | 2.4 | 4.4 | 1.6 | 1.2 | 4.5 | 2.2 | 1.5 |
| Rate of decrease | 0% | 43.0% | 4.3% | 24.0% | 20.0% | 4.3% | 18.5% | 21.0% |

The results in Tables 1 and 2 show that the surfaces of the tubes of the examples had high lubricity, good durability, and quite a low rate of decrease in lubricity. In contrast, the untreated tube of Comparative Example 1 exhibited very poor lubricity, and the commonly used product of Comparative Example 2 had moderately high initial lubricity but exhibited low durability and quite a high rate of decrease in lubricity. Further, in the examples, since the radical polymerization was carried out in the presence of an alkali metal salt such as NaCl or KCl, good lubricity and good durability were obtained even with a polymerization time that did not provide lubricity when no alkali metal salt was present. Thus, more economically advantageous production was achieved in the examples (e.g. comparisons between Example 1 and Comparative Example 4, between Example 4 and Comparative Example 5, and between Example 8 and Comparative Example 7).

The above results demonstrated that sufficient lubricity and sufficient lubricant durability can be simultaneously imparted to the surface of vascular catheters or other objects by forming polymer chains on the surface from a monomer such as potassium 3-sulfopropyl methacrylate, 2-methacryloyloxyethyl phosphorylcholine, or 2-(methacroyloxy)ethyl trimethylammonium chloride in the presence of an alkali metal salt.

The invention claimed is:

1. A method for surface-modifying an object made of a rubber vulcanizate or a thermoplastic elastomer, the method comprising:
    step 1 of forming polymerization initiation points on a surface of the object; and
    step 2 of radically polymerizing a monomer starting from the polymerization initiation points by irradiation with ultraviolet light having a wavelength of 300 to 400 nm in the presence of an alkali metal salt to grow polymer chains on the surface of the object,
    wherein the thermoplastic elastomer is at least one selected from the group consisting of nylon, polyester, polypropylene, acrylonitrile-butadiene-styrene copolymer resin, and dynamically crosslinked thermoplastic elastomers prepared from these elastomers,
    wherein the rubber vulcanizate is at least one selected from the group consisting of natural rubber, deproteinized natural rubber, styrene-butadiene rubber, polybutadiene rubber, polyisoprene rubber, butyl rubber, and halogenated butyl rubber, and
    wherein the duration of the irradiation is 3 to 120 minutes.

2. The method according to claim 1, wherein the step 1 comprises adsorbing a photopolymerization initiator onto a surface of the object, optionally followed by irradiation with ultraviolet light having a wavelength of 300 to 400 nm, to form polymerization initiation points from the photopolymerization initiator on the surface.

3. The method according to claim 2, wherein the photopolymerization initiator is at least one of a benzophenone compound or a thioxanthone compound.

4. The method according to claim 1, wherein the method comprises introducing an inert gas into a reaction vessel, a reaction pipe, and a reaction solution during or before the light irradiation, and polymerizing the monomer in an atmosphere replaced with the inert gas.

5. The method according to claim 1, wherein the monomer is an alkali metal-containing monomer.

6. The method according to claim 5, wherein the alkali metal-containing monomer is at least one selected from the group consisting of alkali metal salts of acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, and styrenesulfonic acid.

7. The method according to claim 1, wherein the monomer is a halogen-containing monomer.

8. The method according to claim 7, wherein the halogen-containing monomer is a nitrogen-containing monomer.

9. The method according to claim 8, wherein the nitrogen-containing monomer is at least one of 2-(methacryloyloxy) ethyl trimethylammonium chloride or 2-(acryloyloxy)ethyl trimethylammonium chloride.

10. The method according to claim 1, wherein the monomer is a zwitterionic monomer.

11. The method according to claim 1, wherein the alkali metal salt is at least one of sodium chloride or potassium chloride.

12. The method according to claim 1, wherein a solution of the monomer, or the monomer in the liquid state contains a polymerization inhibitor, and is polymerized in the presence of the polymerization inhibitor.

13. The method according to claim 1, wherein the duration of the irradiation is 10 to 60 minutes.

14. A method for surface-modifying an object made of a rubber vulcanizate or a thermoplastic elastomer, the method comprising step I of radically polymerizing a monomer starting from polymerization initiation points on a surface of the object by irradiation with ultraviolet light having a wavelength of 300 to 400 nm in the presence of a photopolymerization initiator and an alkali metal salt to grow polymer chains on a surface of the object, wherein the thermoplastic elastomer is at least one selected from the group consisting of nylon, polyester, polypropylene, acrylonitrile-butadiene-styrene copolymer resin, and dynamically crosslinked thermoplastic elastomers prepared from these elastomers, wherein the rubber vulcanizate is at least one selected from the group consisting of natural rubber, deproteinized natural rubber, styrene-butadiene rubber, polybutadiene rubber, polyisoprene rubber, butyl rubber, and halogenated butyl rubber, and wherein the duration of the irradiation is 3 to 120 minutes.

* * * * *